United States Patent [19]

Le Minor

[11] 3,992,521

[45] Nov. 16, 1976

[54] IMMUNOLOGICAL PRODUCT FOR THE TREATMENT OF INTESTINAL INFECTIONS DUE TO PATHOGENIC ENTEROBACTERIA OF THE INFANT

[75] Inventor: Léon Le Minor, Paris, France

[73] Assignee: Etablissement Public: Agence Nationale de Valorisation de la Recherche Anvar, Nevilly-sur-Seine, France

[22] Filed: July 6, 1973

[21] Appl. No.: 377,153

[30] Foreign Application Priority Data

July 7, 1972 France .............................. 72.24696

[52] U.S. Cl. ................................................. 424/87
[51] Int. Cl.$^2$.......................................... A61K 39/40
[58] Field of Search ....................................... 424/87

[56] References Cited
UNITED STATES PATENTS 2,607,716   8/1952   Link....................................... 424/87

OTHER PUBLICATIONS

Levy et al., *Nouv. Presse Med.* vol. 2, p. 1520, June 2, 1973.

Svendsen et al., *Am. J. Vet. Res.*, vol. 32, pp. 899–904, June 1971.

*Primary Examiner*—Shep K. Rose
*Attorney, Agent, or Firm*—Burgess, Dinklage & Sprung

[57] ABSTRACT

An immunological product for the treatment of intestinal infections due to enterobacteria pathogenic to the infant.

It consists of a serum of a horse hyperimmunized by means of cultures of enterobacteria pathogenic to the infant, of the type *Echerichia coli* and *Salmonella*, the serum being administered per os.

This preventive or curative treatment by immunological means makes it possible to avoid the use of antibiotics, which have drawbacks and risks.

21 Claims, No Drawings

IMMUNOLOGICAL PRODUCT FOR THE TREATMENT OF INTESTINAL INFECTIONS DUE TO PATHOGENIC ENTEROBACTERIA OF THE INFANT

The present invention is the result of work carried out in the Service of Enterobacteria at the Pasteur Institute. It relates to the preventive and/or curative treatment of certain intestinal infections affecting man, and more particularly the yound child and infant.

It is known that certain enterobacteria are pathogenic to infants and can cause them to suffer from febrile diarrhoea. Up to now said infections have been treated with antibiotics or associations of antibiotics, but the harmful side-effects of these medicaments, which in certain cases may be extremely serious, and which destroy a large part of the intestinal flora and can thus affect the host and its defense mechanisms, are known. The use of antibiotics in preventive treatments is unreasonable and dangerous. Furthermore, many strains of bacteria have acquired resistance to antibiotics.

An essential object of the invention is a medicament enabling this type of infection to be treated successfully without having to resort to antibiotics, thus avoiding the drawbacks and risks associated therewith.

Another object of the invention is a product for immunological treatment which can be used as a preventive, thus providing considerable advantages, for example in the treatment of populations of infants and young children in which certain subjects are contaminated.

A further object of the invention is a product for immunological treatment which can be administered per os, and thus do away with the drawbacks of administration by the parenteral way of an antiserum prepared on an animal.

The invention relates to a product for immunological treatment consisting of a serum from a horse hyperimmunized by means of enterobacteria cultures pathogenic to the infant.

To the applicant's knowledge, an antiserum has as yet never been used for the treatment of intestinal infections of the infant. The specific nature of the enterobacteria involved in said infections, as well as that of the subjects, should be stressed. Enterobacteria which are not pathogenic to animals may be pathogenic to man. Furthermore, certain enterobacteria which are pathogenic to infants do not cause intestinal infections in adults. As an example, antisera have already been proposed for piglets or young mice, but in both these cases the pathogenic strains were very different from the strains pathogenic to the infant. Thus, H. W. SMITH and M. A. LINGWOOD in their article "The effect of antisera in protecting pigs against experimental E. COLI diarrhoea and oedema disease." J. Med. Microb. 1971, 4, 487–493, describe a serum administered to piglets by the parenteral way. I. KETUI's article "Passive Schutz versuche gegen die Infektion mit dem für Sauglingsmaüse Pathogen E. Coli 0 101: K30 stamm," describes a serum which can be administered per os to young mice, and this in the case of a very special strain of Escherichia coli. In this connection, so called polyvalent antisera have already been proposed prepared from enterobacteria strains pathogenic to bovines, lambs and pigs. The corresponding serotypes of E. Coli and/or Salmonella are very different from those found in infants.

Furthermore, all veterinary products are administered by the parenteral way which, in man, risks causing sensitization accidents.

The particular chracteristics of the colibacilli involved in epidemics affecting infants should be stressed. As an example, most of the enteropathogenic E. Coli in calves possess the K 88 antigen whereas this does not exist in the enteropathogenic E. Coli of infants. E Coli are very varied types of colibacilli differing greatly one from the other. In this connection, it is known that the typhoid bacillus is only pathogenic to the human race. A suspension of typhoid bacilli administered intraveneously to a rabbit induces no particular effect in the receiving animal. It is practically the same for strains of Salmonella.

A fundamental characteristic of the present invention is the use of types of enterobacteria which are practically specific to the human race, which differ from enterobacteria inducing the infections from which animals suffer.

The object of the invention is therefore an immunologic product comprising serum of a horse hyperimmunized by means of enterobacterial cultures pathogenic to the infant, the said serum containing antibodies intended to treat the intestinal infections induced in the infant or young child by the said bacteria and being administrable per os.

The extremely favorable results obtained with the invention were in no way foreseen, as it was impossible to know beforehand whether the antibodies would not be entirely destroyed during digestion, as is the case with many immunological products administered per os.

As bacterial strains it is advantageous to use strains of Escherichia coli and/or Salmonella responsable for intestinal infections of infants and young children. The bibliographical references relating to such strains are, for example, the following:

Kaufmann F. "The bacteriology of Enterobacteriaceae" publisher Munsksgaard, Copenhagen 1966.

Edwards P. R. and W. H. EWING "Identification of Enterobacteriaceae." 3rd Edition, Burgess Publisher, Minneapolis 1972.

Le Minor L. Laboratory diagnostic of Gram negative l bacilli. Enterobacteria, 4th edition. Published by La Tourelle (94) St Mandre 1972.

Thus, according to the invention, the product which can be used as a medicament can be an anti-Escherichia coli serum, an anti/ Salmonella serum or a mixture of these two sera. In the last case a polyvalent serum anti-Salmonella — E.Coli, enteropathogenic to the infant, is obtained, usable in the prevention and treatment of the enteric diseases dependant on these etiologies.

As strains usable for the requirements of the invention may be mentioned, by way of illustration, freshly isolated bacterial strains harboring plasmids responsable to antibiotics for their resistance. Said strains are, on the one hand, Escherichia coli having the following O and K antigens:

| | | | |
|---|---|---|---|
| 0 | 111 : $k_{58}(B_4)$ | 0 119 : $k_{69}(B_{14})$ |
| 0 | 55 : $k_{59}(B_5)$ | 0 124 : $k_{72}(B_{17})$ |
| 0 | 26 : $k_{60}(B_6)$ | 0 125 : $k_{70}(B_{15})$ |
| 0 | 86 : $k_{61}(B_7)$ | 0 126 : $k_{71}(B_{16})$ |
| | | 0 127 : $k_{63}(B_8)$ |

All said strains have recently been isolated. The serotype 0 111: $k_{58}(B_4)$ which is involved in more than half of the infections of the infant due to enteropa thogenic E.coli, possesses the antigen $H_2$, gives a positive reaction to phenylpropionic acid, is resistant to: ampicillin, streptomycin, kanamycin, chloramphenicol, tetracycline and sulfamides. The 0 86: $k_{61}(B_7)$ serotype is resistant to ampicillin and kanamycin, the serotype 0 127: $k_{63}(B_8)$ to streptomycin, chloroamphenicol, tetracycline, sulfamide.

Said strains are, on the other hand, the following serotypes of Salmonella, the most frequently involved in epidemic infectious diarrhoeas due to said bacteria:

Salmonella typhi-murium (1, 4, 5, 12:1 : 1, 2)
Salmonella wien (4, 12: b: 1, w)
Salmonella panama (1, 9, 12 : 1, v. 1, 5)
Salmonella infantis (6, 7 : r: 1, 5)

The strains to be used completely in case of need are enteropathogenic Escherichia coli belonging to other serotypes if their frequency, at present negligible, increased (0 124 : B 17 for example), as well as other serotypes of Salmonella comparable with the four above-mentioned serotypes if they present a risk of causing an epidemic among infants.

The strains given above and used for immunizations are conserved in the collection of the Enterobacteria Services of the Pasteur Institute. It should however be emphasized that the invention is not limited to the use of such strains, as it is generally speaking applicable to the whole class of enterobacteria pathogenic to the infant and young child.

In order to culture the bacteria necessary for the preparation of the serum according to the invention, it is possible to operate according to the usual culture methods. By way of illustration, the following is a technique which has given good results:

Pure strains are cultured separately in Roux boxes containing peptonic agar meat broth. After incubation for 18 to 24 hours at 37° C, the bacteria are recovered in normal saline solution, killed by heating for 1 hour in a water bath at 55° – 60° C and titered with a nephelometer, compared with a reference curve and brought to 10 thousand million bacteria per milliliter.

Immunization of a horse can be effected in accordance with the general techniques of immunization. A mode of embodiment suited to the process will be given as an example:

The amounts to be injected to the horse are administered by subcutaneous injection at progressively larger doses according to the following procedure:

| | |
|---|---|
| 2.5 ml of suspension | + 2.5 ml Freund's adjuvant |
| 5 | + 5 |
| 7,5 | + 5 |
| 10 ml of suspension | + 5 ml Freund's adjuvant |
| 20 | + 5 |
| 30 | + 5 |
| 40 | + 5 |
| 60 | + 5 |
| 80 | + 5 |
| 100 | + 5 |

Mixtures of bacterial 1 suspension and Freund's adjuvant are prepared immediately before the injections. These are given at 2 day intervals for volumes smaller than 50 ml and 3 day intervals for those greater than 50 ml; in other words, they are effected three times a week in the first case and twice a week in the second.

These volumes are given by way of guidance: if, after an injection, the reaction of the horse is too violent, the volume injected will be decreased the next time, and then the progression will be started again. This first series of injections is followed, in the case of Escherichia coli, by four subcutaneous injections of 1, 2, 5 and 10 ml of live suspension having the same bacteria contents as indicated above. The animals are bled 5 to 10 days after the last injection, left to rest for 1 week, then retreated with the same doses of 1, 2 5 and 10 ml of live suspension. In the case of Salmonella the first series of subcutaneous injections with the adjuvant is followed by four subcutaneous injections of 50, 75, 100 and 150 ml killed cultures without an adjuvant, after which the horses are bled, put to rest and reimmunized according to the same procedure. A particularly original characteristic of the process of the invention will be noted in the case of E. coli, according to which immunization with killed bacteria is followed by a final immunization with living bacteria, making it possible to obtain antibodies against antigens which would be destroyed during treatment of bacteria by chemical or thermal means, such as are used to sterilize the bacteria suspension. In the case of Salmonella, the bacteria are first subjected to the action of ultra-sonic waves, which permits about 99% of them to the killed, after which a 2% formol solution is added to the bacterial suspension to finish killing the last living bacteria.

For presentation the sera are collected, filtered through a membrane and put into sterile ampules. Testing of sterility is effected by culture in aerobic and anaerobic conditions. The sera may subsequently be fractionated to isolate the purified globulines therein. A form of medicinal dosage unit consists of sterile ampules having a volume of 2 ml.

The new medicaments of the invention can be administered as they are, per os. For infants they may advantageously be mixed with the feeds. The average dose to provide for corresponds to a dose of 2 ml/kg/24 hours. It is generally thought that a minimum of two 2 ml ampules per day should be administered. As is seen from the results of clinical trials given below, no undesirable side-effects were observed.

The results of these trials show, on the contrary, that the invention provides a selective therapy, with no dangers, for treating infections due to enteropathogenic bacteria in the infant and young child.

The components of the sera according to the invention can be characterized by means of the usual techniques. The agglutinins present in the product can thus be titered: for anti-E.coli sera anti O and K antibodies are titered, whereas for anti-Salmonella sera anti O and H antibodies are titered. Another method of characterization consists of a precipitation in an agar medium with respect to antigens extracted from corresponding cultures by ultrasonic treatment according to the conventional techniques of Outcherlony and immunoelectrophoresis. The following articles may be cited as bibliographic references on immunodiffusion for characterization of antigens.

J. HOLMGREN, G. EGGERTSEN, L. A. HANSON, K. LINCOLN Immunodiffusion studies on E. coli, Acta path. microbScand. 1969, 76, 304–318.

O. GRADOS and W. H. EWING. Technics for characterization of soluble antigens, Monographie Communicable Disease Center. Atlanta. USA December 1969.

J. GRABAR and A. KOSTIC Study by immunoelectrophorectic analysis of sera of vaccinated patients suffering from typhoid, Ann. Inst. Pasteur 1963, 105, 706–724.

They may also be mentioned the book by FASQUELLE, BARBIER, DAGUET and GOULLET "General elements of immunology" Published by Masson (Paris) 1965, notably the chapters "Precipitation in agar medium" p. 279 and the following pages, and "Immunoelectrophoresis" page 238 and the following pages.

Immunological methods make it possible to check the presence of antibodies corresponding to the antigens of the bacteria used for immunization.

The results of clinical trials which were obtained with anti-*Escherichia coli* sera will be given below in order to illustrate the invention. Hereinbelow the product according to the invention will be designated by the abbreviation "anti-coli serum." Said serum was obtained by the general technique of immunization previously described.

CLINICAL TRIALS

Patients treated with anti *E. coli* antibodies. (anti-coli serum)

75 children were treated; they were all less than 18 months old except for two, aged respectively 3 and 2 years.

53 subjects carried *E. Coli* 0 111: $B_4$, 7 *E. coli* 0 55: $B_4$ and 15 *E. coli* 0 26: $B_6$. By simple dyspepsia in the tables which follow there is meant diarrhoea with vomiting without dehydration. Dyspepsia is said to be serious when, in addition to digestive troubles, signs of dehydration are present.

The only treatment, apart from a hydric diet, intravenous perfusion of glucose and electrolytes (in three cases) and restarting feeding in all cases where they were necessary, was the preparation of anti-bodies by the administration of the anti-coli serum.

The serum was administered for 12 days at a dose of 2 to 6 ampules per day according to weight (2 ampules for children weighing less than 4 kg, 4 ampules for children of 4 to 6 kg, 6 ampules for those weighing more), given per os, put in the feeds.

The search for horse Gamma-globulins in stools

The extract of stools was prepared in the following manner: stools were ground in a mortar and a phosphate buffer (0.1 M pH 7 $K_2PO_4$) was added until a soft consistency was obtained. The mixture was left to stand for 24 hours in a cold chamber, then centrifuged for 1.5 hours at 15,000 r.p.m. The supernatant with added "Merseptyl" is kept at + 4° C. Said extract, placed in the cup of an Ouchterlony box, reacts with a horse anti-gamma-globulin serum (Pasteur Institute). The precipitation curve is seen to be identical to that obtained with the globulin fractions of horse serum ("purified" anti-tetanus serum).

BACTERIOLOGICAL TESTS

Systematic tests to detect *E. coli*, *Salmonella* and *Shigella* were carried out when all infants were admitted. Check tests were effected twice a week. In the case of all the children harboring pathogenic *E. coli*, the disappearance of specific germs was confirmed by a second coproculture carried out at least 48 hours after the first which gave a negative result.

CONTROLS

These were selected during the same epidemics as those affecting the patients treated. They were of the same age as the latter.

106 controls were used, 82 harboring *E. coli* 0 111: $B_4$, 8 *E. coli* 0 55: $B_5$ and 16 *E.coli* 0 26: $B_6$.

The hydric diet, restarting of feeding and perfusion, when they were necessary, were performed according to the same rules as with the subjects treated with the anti-coli serum antibodies.

All received antibiotics: 54 children had a single antibiotic (11 Gentalin, 35 Colistin at the normal dose, that is to say, 125,000 units/kg of weight and per day, six received Colistin at a dose of 250,000 units/kg of weight and per day, one had Humatin and one ampicillin), the others were treated with an association of antibiotics comprising:

| | |
|---|---|
| Colistin + Gentalin | 33 times |
| Colistin + Neomycin | five times |
| Colistin + Neomycin + Gentalin | once |
| Colistin + Furadoine | seven times |
| Colistin + Chloramphenicol | twice |
| Colistin + Ampicillin | once |
| Humatin + Gentalin | once |
| Humatin + Colistin | once |
| Streptomycin + Gentalin | once |

The denominations used above for antibiotics are current and referenced, for example, in "The Merck Index" 7th edition, 1960, published by Merck & Co. Inc. Rahway, N. J. USA and in the Vidal dictionary, 1972, Ed. O.V.P. (France).

Results

These are given based on bacteiological criteria. They are said to be excellent when sterilization of stools is obtained in less than 9 days, good when this is observed before the 13th day, bad when it occurs later, that is to say, after treatment by antibodies has been stopped.

The clinical results were equivalent in the two series studied: digestive complaints always regressed in 2 to 4 days.

From the bacteriological point of view, tables I and II show the results obtained with patients treated with the antibodies of the serum anti-coli and with controls treated with antibiotics. The percentages of each category based on the total number of subjects infected with *E. coli* 0 111: $B_4$ are given in brackets.

Statistical analysis (test comparing two observed percentages) was carried out in cases where the number of subjects made this possible. The statistical test can thus be applied to children harboring *E. coli* 0 111: $B_4$, healthy germ carriers, or those suffering from simple dyspepsia with whom excellent results were recorded. There is no significant difference between those treated with antibodies and those who had been given antibiotic (=0.74) for healthy carriers, = 1.06 for cases of simple dyspepsia). For *E. coli* 0 26: $B_6$ both tables (treated patients and controls) are practically identical.

Referring the results to the weight of stools treated, an average amount of gamma-globulins corresponding to 0.015 ml of the serum ingested is found per gram of stool.

Prevention trials

The preventive effects of anti-*E. coli* antibodies were tested during successive epidemics of *E. coli* 0 111: $B_4$. The studies were conducted in two completely comparable infants' wards (same arrangements of the locality, same number of children, same rules of hygiene, same modes of contamination by the infection, same germ). The epidemics started every time with subjects suffering from diarrhea who had just been admitted into each of the two wards. In one ward, antibodies (anti-coli serum) were administered to all the children, in the other the children received no preventive treatment. In the ward where antibodies were given, two children out of 54 were contaminated whereas much contamination was observed in the other ward (14 children out of 21 during the first epidemic, 13 out of 19 during the second, 11 out of 17 during the third, making a total of 38 children out of 57). Both children who escaped the preventive action of the antibodies showed signs of gastero-enteritis of moderate intensity, without particular clinical manifestations compared with the other patients, the same time being allowed for negativation of the coprocultures. In another infants' ward, immunoprevention was introduced when 4 infants out of 11 had *E. Coli* 0 111: $B_4$ diarrhea. No new contamination was observed after this. The preventive action of anti-*E. coli* antibiotics is therefore very effective.

Tolerance

Criteria: tolerance to the medicament was assessed by surveillance of the clinical state of the child, by hemogram, urinary examinations (glycosuria, albuminuria, precipitate), levels of urea in the blood, glycemia electrolytes, the determination of pH and the alkaline reserve. No modification of these parameters was observed during the treatment. Digestive tolerance to the product is excellent.

After administration of antibodies had been stopped, and in 55 subjects receiving anti-*E. coli* antibodies, either preventively or as a treatment, cutaneous sensitization tests were also effected, with intradermic injections of 1/10ml of progressively increasing dilutions of antibodies (from 1/10,000 to 1/10). No child had a positive reaction.

Observations

As the efficiency of the antibody preparation on enteral infections of *E. coli* 0 111: $B_4$, 0 55: $B_5$ and 0 26: $B_6$ (which are very widespred strains) was approximately the same as that of antibiotics, the use of said antibodies in treatment has various advantages compared with these antibiotics: the absence of side-effects or complications, consistently good tolerance, more flexible dosage. The same advantages make the possibilities of using antibodies for prevention particularly interesting, notably in periods of epidemics in communities of infants.

These advantages are connected with the mode of action of the antibodies. The activity of the latter is specific with respect to the corresponding bacterial antigens. The other germs of the intestinal flora are not involved.

TABLE I

| Nature of the infection | RESULTS | Patients treated with the serum | | | | | |
|---|---|---|---|---|---|---|---|
| | | Excellent | | Good | | Bad | |
| | | No. | % | No. | % | No. | % |
| E.COLI 0 111 : $B_4$ | Healthy carriers | 15 | (28.3) | 1 | (1.8) | 6 | (11.3) |
| | Simple dyspepsia | 20 | (37.7) | 3 | (5.6) | 4 | (7.5) |
| | Serious dyspepsia | 2 | (3.7) | 2 | (3.7) | | |
| E.COLI 0 55 : $B_5$ | Healthy carriers | 2 | | | | 1 | |
| | Simple dyspepsia | 3 | | | | | |
| | Serious dyspepsia | 1 | | | | | |
| E. COLI 0 26 : $B_6$ | Healthy carriers | 4 | | | | 1 | |
| | Simple dyspepsia | 6 | | 1 | | 2 | |
| | serious dyspepsia | 1 | | | | | |
| | | | | about 81 % | | about 19% | |

TABLE II

| Nature of the infection | Results | Excellent | | Good | | Bad | |
|---|---|---|---|---|---|---|---|
| | | No. | % | No. | % | No. | % |
| E.COLI 0 111 : $B_4$ | Healthy carriers | 19 | (23.1) | 4 | (4.8) | | |
| | Simple dyspepsia | 24 | (29.2) | 17 | (20.7) | 10 | (12.1) |
| | Serious dyspepsia | 5 | (6.0) | | | 3 | (3.6) |
| E.COLI 0 55 : $B_5$ | Healthy carriers | | | | | | |
| | Simple dyspepsia | 7 | | | | 1 | |
| | Serious dyspepsia | | | | | | |
| E.COLI 0 26 : $B_6$ | Healthy carriers | 5 | | 1 | | 1 | |
| | Simple dyspepsia | 6 | | 1 | | 2 | |
| | Serious dyspepsia | | | | | | |
| | | | | about 84% | | about 16% | |

Conclusion

The preceding results demonstrate that treatment with the serum according to the invention provides results which are at least as good as those recorded with antibiotics. With respect to the latter, the new medicaments have the advantage of not causing side-effects and of being effective even with bacteria which are already resistant to antibiotics. The preventive action of the product of the invention was verified during epidemic outbreaks. Tolerance to the product was excellent, no sensitization was observed.

The invention has been illustrated by clinical trials with respect to anti-*Escherichia coli* serum. Equivalent results are, however, obtained with anti*Salmonella sera*, or with mixed sera when corresponding bacteria are responsible for infections. It is, moreover possible, as a man of the art will easily understand, to bring many variants to the invention without departing from its scope.

I claim:

1. A process for obtaining an immunological product containing antibodies effective to control intestinal infections induced in the human infant or young child by enterobacteria pathogenic to same, consisting essentially in preparing suspensions containing the said enterobacteria, immunizing a horse by injecting it subcutaneously with progressively increasing doses of said suspensions admixed with an adjuvant starting with about 2.5 ml of said suspensions, each injection being separated from the following by a rest period during which the horse receives no injection then, after the last subcutaneous injection, effecting on the same horse subcutaneous injections of said suspensions of bacteria but without an adjuvant, and after a long rest period after the last injection bleeding the horse, to obtain the serum which, in the form of drinkable sterile ampuler constitutes the desired active immunological product.

2. The process of claim 1 wherein suspensions containing about 10 thousand million of said enterobacteria per milliliter are prepared.

3. The process of claim 1 wherein a Freund's adjuvant is used as an adjuvant.

4. The process of claim 1 wherein suspensions of *Escherichia coli* pathogenic to the infant and young child are prepared, in which case the first series of subcutaneous injections with an adjuvant is effected with suspensions of killed *Escherichia coli* enterobacteria, whereas the second series of subcutaneous injections without an adjuvant is effected with suspensions of living *Escherichia coli* enterobacteria.

5. The process of claim 1 werein Escherichia coli having the following O and K antigens are used

| 0 | 111 : $k_{58}$ ($B_4$) | 0 119 : $k_{69}$ ($B_{14}$) |
| 0 | 55 : $k_{59}$ ($B_5$)  | 0 124 : $k_{72}$ ($B_{17}$) |
| 0 | 26 : $k_{60}$ ($B_6$)  | 0 125 : $k_{70}$ ($B_{15}$) |
| 0 | 86 : $k_{61}$ ($B_7$)  | 0 126 : $k_{71}$ ($B_{16}$) |
|   |                        | 0 127 : $k_{63}$ ($B_8$)    |

6. The process of claim 1 wherein pathogenic *Escherichia coli* enterobacteria are used.

7. The process of claim 6 wherein suspensions of *Escherichia coli* 0 124: $B_{17}$ are used.

8. The process of claim 1 wherein the said serum taken from the horse is filtered through a membrane and divided into sterile ampules.

9. Immunological product comprising drinkable sterile ampules of horse serum hyperimmunized by means of enterobacteria cultures pathogenic to the human infant and young child, prepared in accordance with the process of claim 1, the said serum containing an effective amount of specific antibodies controlling the said enterobacteria.

10. The product of claim 9 wherein the said serum contains antibodies to *Escherichia coli*.

11. The product of claim 9 wherein the said serum contains antibodies corresponding to *Escherichia coli* having the following O and K antigens:

| 0 | 111 : $k_{58}$ ($B_4$) | 0 119 : $k_{69}$ ($B_{14}$) |
| 0 | 55 : $k_{59}$ ($B_5$)  | 0 124 : $k_{72}$ ($B_{17}$) |
| 0 | 26 : $k_{60}$ ($B_6$)  | 0 125 : $k_{70}$ ($B_{15}$) |
| 0 | 86 : $k_{61}$ ($B_7$)  | 0 126 : $k_{71}$ ($B_{16}$) |
|   |                        | 0 127 : $k_{63}$ ($B_8$)    |

12. The product of claim 9 wherein the said serum contains antibodies corresponding to pathogenic *Escherichia Coli* enterobacteria.

13. The product of claim 12 wherein the said serum contains antibodies corresponding to the strain *Escherichia coli* 0 124: $B_{17}$ 14. A process for the preventive and curative treatment of intestinal infections induced in the human infant or young child by enterobacteria pathogenic to it, consisting in administering per os to the subject to be trated an effective amount of at least about 4 ml per infant per day of an immunological product in drinkable sterile ampules comprising serum from a horse hyperimmunized by means of suspensions of said enterobacteria, the said serum containing specific antienterobcteria antibodies prepared in accordance with claim 1.

15. The process of claim 14 wherein the said serum contains antibodies to *Escherichia coli*.

16. The process of claim 14 wherein the said serum contains antibodies corresponding to *Escherichia coli* having the following O and K antigens:

| 0 | 111 : $k_{58}$ ($B_4$) | 0 119 : $k_{69}$ ($B_{14}$) |
| 0 | 55 : $k_{59}$ ($B_5$)  | 0 124 : $k_{72}$ ($B_{17}$) |
| 0 | 26 : $k_{60}$ ($B_6$)  | 0 125 : $k_{70}$ ($B_{15}$) |
| 0 | 86 : $k_{61}$ ($B_7$)  | 0 126 : $k_{71}$ ($B_{16}$) |
|   |                        | 0 125 k :$_{63}$ ($B_8$)    |

17. The process of claim 14 wherein the said serum contains antibodies corresponding to pathogenic *Escherichia coli* enterobacteria.

18. The process of claim 17 wherein the said serum contains antibodies corresponding to strain *Escherichia coli* 0 124: $B_{17}$.

19. The process of claim 14, wherein drinkable sterile ampules containing the said serum are administered.

20. The process of claim 19 wherein drinkable sterile ampules containing 2 ml of said serum are administered.

21. The process of claim 19 wherein at least two drinkable sterile ampules containing 2 ml of said serem are administered daily.

* * * * *